United States Patent [19]

Cavazza

[11] 4,237,167

[45] Dec. 2, 1980

[54] ACYL-CARNITINES IN A THERAPEUTICAL METHOD FOR TREATING CHRONIC URAEMIC PATIENTS UNDERGOING REGULAR DIALYSIS AND LIQUID COMPOSITION FOR USE THEREIN

[76] Inventor: Claudio Cavazza, 35, Via Marocco, 00144 Rome, Italy

[21] Appl. No.: 39,233

[22] Filed: May 15, 1979

[30] Foreign Application Priority Data

May 15, 1978 [IT] Italy ............................. 49355 A/78

[51] Int. Cl.³ ........................................... A61K 31/32
[52] U.S. Cl. ................................ 424/311; 424/312; 424/313; 424/314; 424/316
[58] Field of Search ............... 424/311, 312, 313, 314, 424/316

[56] References Cited

PUBLICATIONS

Lancet, Apr. 21, 1979, p. 882.
Chemical Abstracts, 86:137401b, (1977).
Chemical Abstracts, 83:73716m, (1975).
Chemical Abstracts, 82:166032l, (1975).

*Primary Examiner*—Leonard Schankman
*Attorney, Agent, or Firm*—Lester Horwitz

[57] ABSTRACT

A therapeutical method for treating uraemic patients in regular dialysis treatment (RDT) is disclosed, wherein an acyl-carnitine (typically acetyl-carnitine) is administered to the patients. The acyl-carnitine can be administered over the whole treatment period by the oral route exclusively. Alternatively, while oral administration is carried out in those days in which the patient is not subjected to the haemodialytic session, when the patient undergoes dialysis, the acyl-carnitine is administered by slow infusion, or an acyl-carnitine-containing dialyzing liquid is used. Furthermore, a suitable dialyzing solution is also disclosed.

10 Claims, 1 Drawing Figure

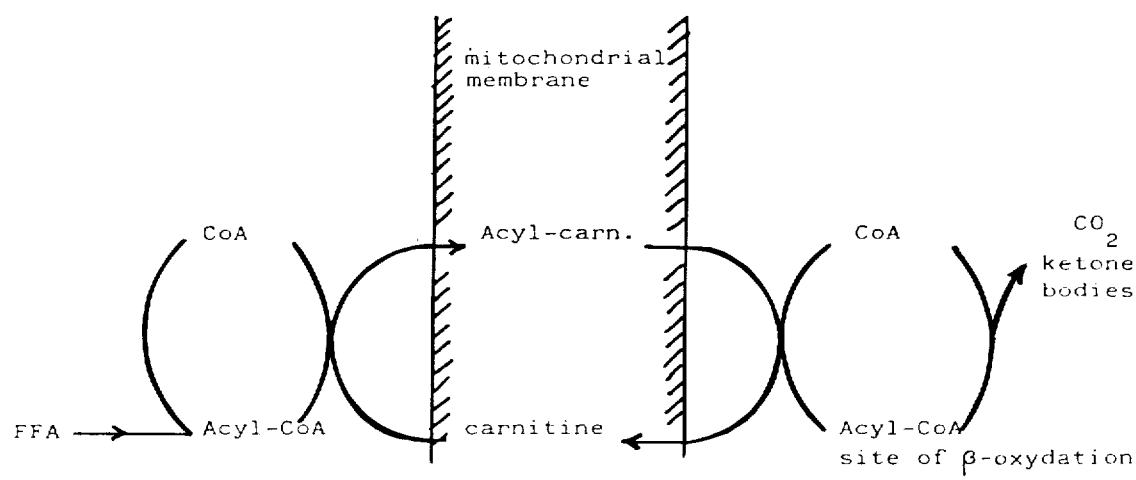

ACYL-CARNITINES IN A THERAPEUTICAL METHOD FOR TREATING CHRONIC URAEMIC PATIENTS UNDERGOING REGULAR DIALYSIS AND LIQUID COMPOSITION FOR USE THEREIN

BACKGROUND OF THE INVENTION

1. Field of the Invention

The present invention pertains to a therapeutical method for the treatment of chronic uraemic patients submitted to haemodialysis and, more particularly, pertains to a therapeutical method compensating or preventing the depletion of carnitine which occurs in subjects affected by chronic uraemia undergoing periodical haemodialysis.

According to another aspect, the present invention pertains to a concentrated polysaline solution and a diluted polysaline solution, obtainable from the former by suitable dilution, adapted for use as the dialyzing liquid in the therapeutical method of the present invention.

2. Description of the Prior Art

It is known that patients affected by chronic uraemia, undergoing periodic haemodialysis, frequently develop myocardiopathies that are inalterable by intensive dialysis, and therefore not attributable to an accumulation of toxic catabolites nor to sodium and water retention. In such patients it is possible to observe a clinical picture known as post-dialytic syndrome, characterized by marked muscular asthenia and a sensation of torpor, particularly evident immediately following dialysis and which may often last even for several hours, so making difficult, if not impossible, a full resumption of working activity.

It has furthermore been found that while the plasma concentration of carnitine in uraemic patients prior to haemodialysis is equal to or slightly lower than the values observed in normal subjects, upon termination of dialysis the concentration of carnitine is reduced to approximately 25% of the pre-dialysis value. It has also been observed that during the period between the termination of one dialytic treatment and the beginning of the next the plasma concentration of carnitine tends to rise and practically reaches, within a few hours, its normal level, but this occurs due to the transfer of carnitine from the tissues to the plasma with attendant progressive tissue depletion. Particularly serious consequences are brought about by carnitine depletion in the myocardium and skeletal muscles.

In addition, it has been observed that there is a significant correlation between reduced carnitine concentration and increased free fatty acid levels in plasma which occur during haemodialysis. In fact, reduced carnitine concentration hinders normal cellular function thus reducing or blocking the oxidation of free fatty acids (FFA) which cannot reach the beta-oxidation sites since they do not cross the mitochondrial membrane as shown by the reaction scheme as set forth in the drawing.

In such conditions there is a shortage of the principal energy supply to the muscular cells, especially the myocardial cells, which use fatty acid as their preferential energy substrate and develop the above-mentioned functional anomalies of the myocardium characterized by rhythm disturbances, contractile force disturbances, etc.

These affections are often encountered in patients submitted to periodical haemodialysis, such as to constitute one of the main risks when performing haemodialytic therapy.

SUMMARY OF THE INVENTION

Therefore it is apparent that the necessity has been felt for a suitable therapeutical means capable of compensating or preventing both the loss of carnitine in plasma during haemodialysis and the depletion of carnitine levels in tissues (particularly the myocardium and skeletal muscles) which occurs in subjects affected by chronic uraemia following periodical haemodialysis repeated over a prolonged period of time.

The object of the present invention is to provide such therapeutical means.

On the basis of the above, it would appear logical that the most efficacious method to compensate the loss of plasma carnitine which takes place in chronic uraemic patients during haemodialysis and the depletion of carnitine in tissues, resulting from repeated haemodialyses, consists in the intravenous administration of carnitine during the haemodialytic session.

This would be logically foreseen, especially since the most immediate and obvious lowering of the level of carnitine occurs in the plasma carnitine, with the maximum difference occuring between predialysis value and that revealed at the end of the dialysis session. In view of the relationship between loss and depletion of carnitine and the state of asthenia presented by the patient, the intravenous administration of carnitine would seem to be the most effective administration route in counteracting also this state of asthenia.

Consequently, it would not seem likely that the administration of compounds other than carnitine might result in a therapeutically effective treatment.

On the other hand, in accordance with the present invention a therapeutic method for the treatment of chronic uraemic patients under periodic haemodialysis has been found which comprises orally administering to such patients, both during the days of haemodialysis session, and during the days between one session and another, 3 to 6 g per day of an acyl-carnitine of the general formula

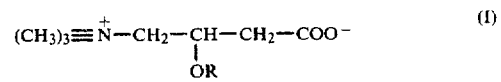

$$(CH_3)_3 \equiv \overset{+}{N}-CH_2-CH-CH_2-COO^- \\ \underset{OR}{|}$$ (I)

wherein R represents acetyl, propionyl, butyryl, hydroxy butyryl, hexanoyl, octanoil, decanoyl, palmitoyl, stearoyl, acetoacetyl, succinyl, isovaleryl and crotonyl or a pharmaceutically acceptable salt thereof.

Throughout this specification, "acyl-carnitine" means an acyl-carnitine of general formula (I).

Surprisingly, it has also been found that in some cases of chronic uraemic patients, if the administration of acyl-carnitine bu the intravenous route is selected, and the intravenous infusion is not carried out following the operating conditions which will be later described, the deep feeling of asthenia presented by such uraemic patients may be aggravated instead of alleviated. In some cases the occurrence of synaptic blockage has been noted, for the removal of which it has been necessary to administered prostigmine.

On the other hand it was found that the uraemic patients undergoing periodic haemodialytic treatment did not experience any objectionable side effect and did not show any signs of asthenia when the administration of acyl-carnitine by the intravenous route was effected by slow infusion during the haemodialytic session.

Therefore, the invention also includes a therapeutic method for treating chronic uraemic patients undergoing periodic haemodialysis, which comprises the following steps:

(1) during the days between one haemodialytic session and the next, orally administering to these patients from 3 to 6 g per day of acyl-carnitine, or a pharmaceutically acceptable salt thereof;

(2) on the days of the haemodialytic session, administering to these patients, during the haemodialytic session from 3 to 6 g of acyl-carnitine or a pharmaceutically acceptable salt thereof, by slow infusion.

On the days of haemodialytic session, acyl-carnitine may also be administered partly by the oral route and partly by slow infusion. In this case, the overall quantity of acyl-carnitine administered shall not exceed approximately 10 g.

"Slow infusion" stands for an infusion in which the solution comprising acyl-carnitine, or any of its pharmaceutically acceptable salts, is administered at the rate of 20 to 40 drops per minute.

The choice of a suitable solvent for acetyl-carnitine, in view of the intended intravenous administration, would be apparent to any one having ordinary skill in this art. Normally, an accurately sterilised saline solution is used.

DESCRIPTION OF THE PREFERRED EMBODIMENT

It was also surprisingly found that particularly favourable therapeutic results are achieved by a method in which acyl-carnitine was administered by the oral route to the patient under haemodialytic treatment only on those days during which the patient was not submitted to a dialytic session, while during the actual dialytic session, a dialyzing liquid containing acyl-carnitine was used.

Such preferred therapeutic method, according to the invention, for the treatment of chronic uraemic patients undergoing haemodialysis, comprises more particularly the following steps:

(1) on the days between one haemodialytic session and the next, orally administering by the oral route to these patients from 3 to 6 g per day of acyl-carnitine or a pharmaceutically acceptable salt thereof;

(2) on the days of haemodialytic session, subjecting these patients to dialysis using, as dialyzing liquid, a solution containing a quantity of acyl-carnitine or a pharmaceutically acceptable salt thereof, sufficient to make the molar concentration of acyl-carnitine in said solution at least equal to the molar concentration of the plasma carnitine of the patient under dialytic treatment.

It was found that by operating in such a manner, it is possible to avoid the loss of plasma carnitine which otherwise takes place during a haemodialytic session, the concentration of plasma carnitine remaining practically unchanged during the dialytic session.

In this manner, it is possible to avoid the tissue carnitine depletion which is the long-term consequence of repeated losses of carnitine the patient undergoes during the successive dialytic sessions he is submitted to over a prolonged period of time.

Although for this purpose it is sufficient that the solution for the haemodialysis be equimolar in acyl-carnitine which respect to the plasma carnitine of the patient under dialytic treatment, it is preferable to use a slightly more concentrated solution.

In practice, the haemodialysis solution contains 50 to 100, preferably 60–80 μmoles/liter of acyl-carnitine or a pharmaceutically acceptable salts.

An illustrative polysaline solution, ready for use in the dialytic treatment of chronic uraemic patients, comprises:

| sodium ions | 140–145 m Eq/l |
|---|---|
| potassium ions | 0.8–1.2 m Eq/l |
| calcium ions | 3.2–3.8 m Eq/l |
| magnesium ions | 1.2–1.8 m Eq/l |
| chlorine ions | 105–115 m Eq/l |
| acetic ions | 35–40 m Eq/l |
| glucose | 0.97–1.03 μ M/l |
| acyl-carnitine or pharmaceutically acceptable salt thereof | 50–100 |

As is known in the haemodialytic technique, concentrated polysaline solutions are available commercially which when suitably diluted provide solutions ready for use.

In accordance with the invention, a concentrated polysaline solution for haemodialysis comprises a quantity of acyl-carnitine or a pharmaceuticaly acceptable salt thereof, sufficient, upon dilution of this solution, to give a diluted polysaline solution ready for use where the acyl-carnitine molar concentrations is at least equal to the molar concentration of the plasma carnitine of the patient under dialytic treatment.

As an example—a concentrated polysaline solution, a liter of which diluted with 34 liters of distilled water gives a solution ready for use, has the following typical composition:

| sodium chloride | 210–215 g/l |
|---|---|
| sodium acetate trihydrate | 178–182 g/l |
| magnesium chloride hexahydrate | 4.8–5.5 g/l |
| calcium chloride hexahydrate | 12.5–14 g/l |
| potassium chloride | 2.5–2.7 g/l |
| anhydrous glucose | 34–36 g/l |
| acyl-carnitine | 1750–3500 μ M/l |

CLINICAL STUDIES

Clinical test have been performed, submitting chronic uraemic patients to treatment according to the present invention. Some clinical cases are subsequently illustrated. A first group of patients (Group A: 5 patients) was treated with placebo for 30 days. A second group of patients (Group B: 5 patients) was treated with acetyl-carnitine for 30 days according to the wholly oral administration method.

The following tests were carried out on the patients of Group A and B (before and after treatment):

(a) electrocardiogramme (b) maximal effort test with a cycloergometer

A computerized Dynavit cycloergometer was used which provides the load (in watts) to which the patient must be submitted, based on body weight and age.

The trial was interrupted either for muscular exhaustion or for over-reaching of the cardiac frequency limits (> H.R.) (this parameter also established by the cycloergometer computer).

(c) neuromuscular condition rate (NMCR)

(d) electromyography (EMG)

This parameter was used in order to assign a precise scientific significance thus rendering measurable the subjective asthenic "sensation" so frequently experienced by patients undergoing periodic haemodialytic treatment.

The measurements of neuromuscular condition rate and of the electromyography were carried out with MK III Medelek apparatus.

For the interpretation of the electromyograph see for example:

Simpson J. A.
"Control of Muscle in Health and Disease, in Control and Innervation of Skeletal Muscle"
(B. L. Andrew, (1966), p. 171-180), and
Walton J. N.
"Disorders of Voluntary Muscle"
Churchill Livingstone, 3rd edition, (1974) p. 1014-1019.

(e) cardiac diameter measurement.

GROUP A

Case 1

A 48 year old male patient, diagnosed as suffering from chronic renal insufficiency due to diabetic nephropathy, underwent regular dialysis treatment (3 sessions per week of 5 hours each).
Regular dialysis treatment commenced: Oct. 20, 1977.
A placebo was administered to the patient for 30 days.
ECG prior to therapy: Left ventricular overload
ECG after therapy: Left ventricular overload
Physical effort with 100 watt load
  prior to therapy: 1 min. 27 sec. (muscular exhaustion)
  after therapy: 1 min. 35 sec. (muscular exhaustion)
NMCR (neuromuscular conduction rate)
  prior to therapy: 43 m/sec
  after therapy: 42 m/sec
EMG (maximum effort)
  prior to therapy: single obscillations
  after therapy: single obscillations

| CARDIAC DIAMETERS | | |
|---|---|---|
| Type | Prior to therapy | after therapy |
| Longitudinal diameter | 16.0 | 16.0 |
| Basal diameter | 14.4 | 14.5 |
| Transversal diameter | 16.5 | 16.5 |
| Left ventricular chord | 11.5 | 11.5 |
| Left ventricular sagitta | 2.3 | 2.3 |
| Cardiothoracic index | 55% | 55% |

Case 2

A 34 year old female patient, diagnosed as suffering from chronic renal insufficiency due to chronic glomerulonephritis, underwent regular dialysis treatment (3 sessions per week of 4 hours each).
Regular dialysis treatment commenced: Oct. 30, 1977.
A placebo was administered to the patient for 30 days.
ECG prior to therapy: Bordering normal limits
ECG after therapy: Bordering normal limits
Physical effort with 60 watt load
  prior to therapy: 1 min. 36 sec. (muscular exhaustion)
  after therapy: 1 min. 30 sec. (muscular exhaustion)
NMCR (neuromuscular conduction rate)
  prior to therapy: 47 m/sec
  after therapy: 47 m/sec
EMG (maximum effort)
  prior to therapy: subinterferential
  after therapy: subinterferential

| CARDIAC DIAMETERS | | |
|---|---|---|
| Type | Prior to therapy | after therapy |
| Longitudinal diameter | 16.7 | 16.7 |
| Basal diameter | 12.5 | 12.5 |
| Transversal diameter | 15.8 | 16.0 |
| Left ventricular chord | 12.2 | 12.2 |
| Left ventricular sagitta | 1.9 | 1.9 |
| Cardiothoracic index | 60% | 61% |

Case 3

A 24 year old male patient, diagnosed as suffering from chronic renal insufficiency due to chronic glomerulonephritis, underwent regular dialysis treatment (3 sessions per week of 4 hours each).
Regular dialysis treatment commenced: Dec. 7, 1977.
A placebo was administered to the patient for 30 days.
ECG prior to therapy: Bordering normal limits
ECG after therapy: Bordering normal limits
Physical effort with 60 watt load
  prior to therapy: 15 min. 34 sec. (muscular exhaustion)
  after therapy: 15 min. 04 sec. (muscular exhaustion)
NMCR (neuromuscular conduction rate)
  prior to therapy: 51 m/sec
  after therapy: 50 m/sec
EMG (maximum effort)
  prior to therapy: subinterferential
  after therapy: subinterferential

| CARDIAC DIAMETERS | | |
|---|---|---|
| Type | Prior to therapy | after therapy |
| Longitudinal diameter | 13.3 | 13.3 |
| Basal diameter | 11.9 | 11.9 |
| Transversal diameter | 13.0 | 13.0 |
| Left ventricular chord | 9.2 | 9.2 |
| Left ventricular sagitta | 2.2 | 2.2 |
| Cardiothoracic index | 41% | 41% |

Case 4

A 35 year old male patient, diagnosed as suffering from chronic renal insufficiency due to chronic glomerulonephritis, underwent regular dialysis treatment (3 sessions per week of 4 hours each).
Regular dialysis treatment commenced: Oct. 31, 1977.
A placebo was administered to the patient for 30 days.
ECG prior to therapy: Left ventricular overload
ECG after therapy: Left ventricular overload
Physical effort with 60 watt load
  prior to therapy: 14 min. 29 sec. (muscular exhaustion)
  after therapy: 14 min. 00 sec. (muscular exhaustion)
NMCR (neuromuscular conduction rate)
  prior to therapy: 40 m/sec
  after therapy: 40 m/sec
EMG (maximum effort)
  prior to therapy: subinterferential
  after therapy: subinterferential

| CARDIAC DIAMETERS | | |
|---|---|---|
| Type | Prior to therapy | after therapy |
| Longitudinal diameter | 16.2 | 16.5 |
| Basal diameter | 12.2 | 12.4 |
| Transversal diameter | 15.1 | 15.0 |
| Left ventricular chord | 11.7 | 11.7 |
| Left ventricular sagitta | 2.0 | 2.0 |
| Cardiothoracic index | 52% | 52% |

Case 5

A 49 year old male patient, diagnosed as suffering from chronic renal insufficiency due to chronic glomerulonephritis, underwent regular dialysis treatment (3 sessions per week of 4 hours each).
Regular dialysis treatment commenced: Apr. 22, 1977.
A placebo was administered to the patient for 30 days.
ECG prior to therapy: slight left ventricular myocardiopathy
ECG after therapy: slight left ventricular myocardiopathy
Physical effort with 100 watt load
  prior to therapy: 1 min. 34 sec. (muscular exhaustion)
  after therapy: 1 min. 30 sec. (muscular exhaustion)
NMCR (neuromuscular conduction rate)
  prior to therapy: 56 m/sec
  after therapy: 56 m/sec
EMG (maximum effort)
  prior to therapy: subinterferential
  after therapy: subinterferential

| CARDIAC DIAMETERS | | |
|---|---|---|
| Type | Prior to therapy | after therapy |
| Longitudinal diameter | 14.4 | 14.4 |
| Basal diameter | 12.1 | 12.0 |
| Transversal diameter | 14.0 | 14.0 |
| Left ventricular chord | 9.8 | 9.8 |
| Left ventricular sagitta | 1.8 | 1.8 |
| Cardiothoracic index | 45% | 45% |

GROUP B

Case 1

A 21 year old male patient, diagnosed as suffering from chronic renal insufficiency due to chronic pielonephritis, underwent regular dialysis treatment (3 sessions per week of 5 hours each).
Regular dialysis treatment commenced: Sept. 11, 1977.
Acetyl-carnitine (3 g/day) was administered to the patient for 30 days.
ECG prior to therapy: bordering normal limits
ECG after therapy: bordering normal limits
Physical effort with 80 watt load
  prior to therapy: 2 min 57 sec (>HR)
  after therapy: 4 min 28 sec (>HR)
NMCR (neuromuscular conduction rate)
  prior to therapy: 32 m/sec
  after therapy: 40 m/sec
EMG (maximum effort)
  prior to therapy: single obscillations
  after therapy: subinterferential

| Cardiac diameters | | |
|---|---|---|
| Type | prior to therapy | after therapy |
| Longitudinal diameter | 14.4 | 14.2 |
| Basal diameter | 12.2 | 12.0 |
| Transversal diameter | 14.0 | 13.7 |
| Left ventricular chord | 10.1 | 10.0 |
| Left ventricular sagitta | 1.5 | 1.5 |
| Cardiothoracic index | 51% | 50% |

CASE 2

A 56 year old male patient, diagnosed as suffering from chronic renal insufficiency due to chronic glomerulonephritis, underwent regular dialysis treatment (3 sessions per week of 4 hours each).
Regular dialysis treatment commenced: Aug. 10, 1977
Acetyl-carnitine (5 g/day) was administered to the patient for 30 days.
ECG prior to therapy: left ventricular overload, incomplete left branch block
ECG after therapy: left ventricular overload, incomplete left branch block.
Physical effort with 50 watt load
  prior to therapy: 0 min 25 sec (>HR)
  after therapy: 0 min 38 sec (>HR)
NMCR (neuromuscular conduction rate)
  prior to therapy: 37 m/sec
  after therapy: 40 m/sec
EMG (maximum effort)
  prior to therapy: single obscillations
  after therapy: subinterferential

| Cardiac diameters | | |
|---|---|---|
| Type | prior to therapy | after therapy |
| Longitudinal diameter | 16.1 | 15.3 |
| Basal diameter | 12.0 | 11.2 |
| Transversal diameter | 15.0 | 14.5 |
| Left ventricular chord | 11.2 | 11.0 |
| Left ventricular sagitta | 1.8 | 1.7 |
| Cardiothoracic index | 58% | 56% |

CASE 3

A 32 year old male patient, diagnosed as suffering from chronic renal insufficiency due to chronic glomerulonephritis, underwent regular dialysis treatment (3 sessions per week of 4 hours each).
Regular dialysis treatment commenced: Feb. 5, 1978
Acetyl-carnitine (6 g/day) was administered to the patient for 30 days.
ECG prior to therapy: ventricular extrasystoles - left ventricular overload
ECG after therapy: left ventricular overload
Physical effort with 70 watt load
  prior to therapy: 1 min 26 sec (>HR)
  after therapy: 1 min 56 sec (>HR)
NMCR (neuromuscular conduction rate)
  prior to therapy: 40 m/sec
  after therapy: 44 m/sec
EMG (maximum effort)
  prior to therapy: subinterferential
  after therapy: interferential

| Type | Cardiac diameters prior to therapy | after |
|---|---|---|
| Longitudinal diameter | 13.5 | 13.2 |
| Basal diameter | 10.8 | 10.5 |
| Transversal diameter | 12.5 | 12.5 |
| Left ventricular chord | 10.1 | 10.0 |
| Left ventricular sagitta | 1.8 | 1.8 |
| Cardiothoracic index | 46% | 46% |

CASE 4

A 24 year old male patient, diagnosed as suffering from chronic renal insufficiency due to chronic glomerulonephritis, underwent regular dialysis treatment (3 sessions per week of 4.5 hours each).
Regular dialysis treatment commenced: Sept. 11, 1979.
Acetyl-carnitine (3 g/day) was administered to the patient for 30 days.
ECG prior to therapy: bordering normal limits
ECG after therapy: bordering normal limits
Physical effort with 80 watt load
  prior to therapy: 3 min 04 sec (muscular exhaustion)
  after therapy: 4 min 12 sec (muscular exhaustion)
NMCR (neuromuscular conduction rate)
  prior to therapy : 42 m/sec
after therapy: 44 m/sec
EMG (maximum effort )
  prior to therapy: subinterferential
  after therapy: interferential

| Type | Cardiac diameter prior to therapy | after |
|---|---|---|
| Longitudinal diameter | 14.9 | 14.6 |
| Basal diameter | 12.5 | 12.0 |
| Transversal diameter | 15.5 | 14.9 |
| Left ventricular chord | 9.8 | 9.5 |
| Left ventricular sagitta | 2.1 | 2.1 |
| Cardiothoracic index | 52% | 50% |

CASE 5

A 51 year old male patient, diagnosed as suffering from chronic renal insufficiency due to gouty neophropathy, underwent regular dialysis treatment (3 sessions per week of 4 hours each).
Regular dialysis treatment commenced: Dec. 12, 1977.
Acetyl-carnitine (5 g/day) was administered to the patient for 30 days.
ECG prior to therapy: bordering normal limits
ECG after therapy: bordering normal limits
Physical effort with 70 watt load
  prior to therapy: 2 min 03 sec (>HR)
  after therapy: 4 min 20 sec (>HR)
NMCR (neuromuscular conduction rate)
  prior to therapy: 50 m/sec
  after therapy: 50 m/sec
EMG (maximum effort)
  prior to therapy: subinterferential
  after therapy: interferential

| Type | Cardiac diameters prior to therapy | after |
|---|---|---|
| Longitudinal diameter | 14.6 | 14.4 |
| Basal diameter | 11.0 | 11.0 |
| Transversal diameter | 13.9 | 13.6 |
| Left ventricular chord | 7.7 | 7.6 |
| Left ventricular sagitta | 1.7 | 1.7 |
| Cardiothoracic index | 47% | 46% |

What is claimed is:

1. A therapeutical method for treating chronic uraemic patients under regular dialysis treatment, which comprises orally administering to said patients, both on the days of the haemodialysis sessions and on the days between one session and the next one, from 3 to 6 grams/day of an acyl-carnitine of general formula

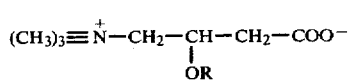

$$(CH_3)_3 \equiv \overset{+}{N}-CH_2-\underset{\underset{OR}{|}}{CH}-CH_2-COO^- \qquad (I)$$

wherein R represents acetyl, propionyl, butyryl, hydroxy butyryl, hexanoyl, octanoyl, decanoyl, palmitoyl, stearoyl, acetoacetyl, succinyl, isovaleryl and crotonyl or a pharmaceutically acceptable salt thereof.

2. A therapeutical method for treating chronic uraemic patients under regular dialysis treatment which comprises the following steps:
   (1) on the days between one haemodialytic session and the next one, orally administering to said patients from 3 to 6 grams/day of an acyl-carnitine of claim 1 or a pharmaceutically acceptable salt thereof;
   (2) on the days of the haemodialytic session, administering to said patients, during the haemodialytic session, from 3 to 6 grams of an acyl-carnitine of claim 1 or a pharmaceutically acceptable salt thereof, by slow infusion.

3. A therapeutical method for treating chronic uraemic patients under regular dialysis treatment, which comprises the following steps:
   (1) on the days between one haemodialytic session and the next one, orally administering to said patients from 3 to 6 grams day of an acyl-carnitine of claim 1 or a pharmaceutically acceptable salt thereof;
   (2) on the days of the haemodialytic session, submitting said patients to dialysis using as dialyzing liquid a dialytic solution comprising an amount of said acyl-carnitine or a pharmaceutically acceptable salt thereof sufficient to make the molar concentration of said acyl-carnitine in said solution at least equal to the molar concentration of the plasma carnitine of the patient under dialytic treatment.

4. The therapeutic method of claim 3, wherein said dialytic solution is equimolar in said acyl-carnitine with respect to the plasma carnitine of the patient under dialytic treatment.

5. The therapeutic method of claim 3, wherein said dialytic solution comprises from 50 to 100μ moles/liter of said acyl-carnitine or a pharmaceutically acceptable salt thereof.

6. A concentrated, polysaline solution for haemodialysis which comprises an amount of an acyl-carnitine of claim 1 or a pharmaceutically acceptable salt thereof sufficient, upon dilution of said concentrated solution, to give a diluted, ready-for-use polysaline solution wherein the acyl-carnitine molar concentration is at least equal to the molar concentration of the plasma carnitine of the patient under dialytic treatment.

7. The concentrated solution of claim 6 which comprises an amount of an acyl-carnitine of formula (I) or a pharmaceutically acceptable salt thereof, sufficient, upon dilution of said concentrated solution, to give a ready-for-use, diluted polysaline solution equimolar in acyl-carnitine with respect to the plasma carnitine of the patient under dialytic treatment treatment.

8. The concentrated solution of claim 6 which comprises an amount of an acyl-carnitine of formula (I) or a pharmaceutically acceptable salt thereof sufficient, upon dilution of said concentrated solution, to give a diluted, ready-for-use polysaline solution, comprising from 50 to 100μ moles/liter of said acyl-carnitine.

9. The concentrated solution of claim 8, comprising:

| | |
|---|---|
| sodium chloride | 210–215 g/l |
| sodium acetate trihydrate | 178–182 g/l |
| magnesium g/l hexahydrate | 4.8–5.5 g/l |
| calcium chloride hexahydrate | 12.5–14 g/l |
| potassium chloride | 2.5–2.7 g/l |
| anhydrous glucose | 34–36 g/l |
| an acyl-carnitine of formula (I) or a pharmaceutically acceptable salt thereof | 1750–3500 μmoles/l |

10. A diluted, ready-for-use polysaline solution for the dialytic treatment of chronic uraemic patients, comprising:

| | |
|---|---|
| sodium ions | 140–145 m Eq/l |
| potassium ions | 0.8–1.2 m Eq/l |
| calcium ions | 3.2–3.8 m Eq/l |
| magnesium ions | 1.2–1.8 m Eq/l |
| chloride ions | 35–40 m Eq/l |
| glucose | 0.95–1.05 m Eq/l |
| an acyl-carnitine of claim 1 or a pharmaceutically acceptable salt thereof | 50–100 μmoles/l |

* * * * *